United States Patent [19]

Fehr et al.

[11] 4,229,451
[45] Oct. 21, 1980

[54] ERGOPEPTINE DERIVATIVES

[75] Inventors: Theodor Fehr, Dornach; Paul Stadler, Biel-Benken, both of Switzerland

[73] Assignee: Sandoz Ltd., Basel, Switzerland

[21] Appl. No.: 920,480

[22] Filed: Jun. 29, 1978

Related U.S. Application Data

[63] Continuation of Ser. No. 626,782, Oct. 29, 1975, abandoned, which is a continuation of Ser. No. 525,780, Nov. 21, 1974, abandoned.

[30] Foreign Application Priority Data

Nov. 28, 1973 [CH] Switzerland ............... 16698/73

[51] Int. Cl.³ ............... A01K 31/495; C07D 519/02
[52] U.S. Cl. ............... 424/250; 544/346; 546/69
[58] Field of Search ............... 544/346; 424/250

[56] References Cited

U.S. PATENT DOCUMENTS

| 2,619,488 | 11/1952 | Stoll et al. | 260/285.5 |
| 3,336,311 | 8/1967 | Hofmann et al. | 544/346 |
| 3,422,110 | 1/1969 | Stadler et al. | 544/346 |
| 3,755,328 | 8/1973 | Stadler et al. | 544/346 |
| 4,091,099 | 5/1978 | Lehr et al. | 544/346 |
| 4,138,565 | 2/1979 | Ehrhardt et al. | 544/346 |

FOREIGN PATENT DOCUMENTS

| 769260 | 3/1957 | United Kingdom | 260/285.5 |
| 1149565 | 6/1966 | United Kingdom | 544/346 |
| 1158265 | 10/1966 | United Kingdom | 544/346 |

OTHER PUBLICATIONS

Fehr et al.; Helv. Chem. Acta. vol. 53 pp. 2197–2201 (1970).

Primary Examiner—Mary C. Lee
Attorney, Agent, or Firm—Gerald D. Sharkin; Robert S. Honor; Thomas O. McGovern

[57] ABSTRACT

This invention provides new compounds of formula I,

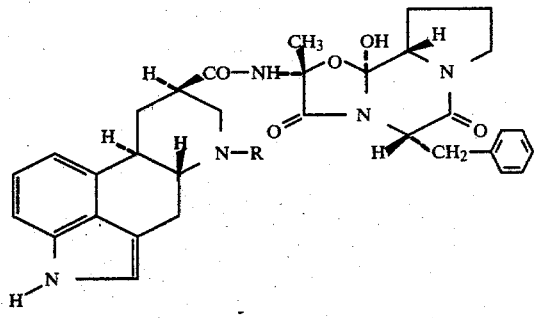

wherein R is branched chain alkyl of 3 to 6 carbon atoms, useful as venoconstrictors and venotonics.

7 Claims, No Drawings

ERGOPEPTINE DERIVATIVES

This is a continuation of Ser. No. 626,782, filed Oct. 29, 1975, now abandoned, which in turn is a continuation of Ser. No. 525,780, filed Nov. 21, 1974, now abandoned.

The present invention relates to new heterocyclic compounds.

In accordance with the invention there are provided new compounds of formula I,

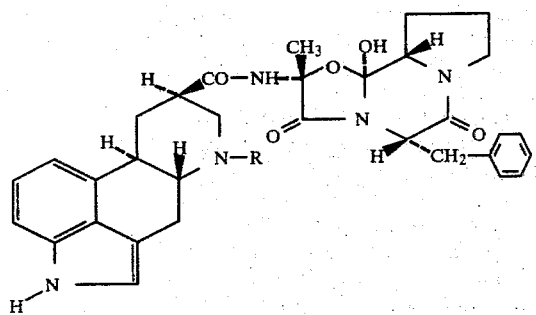

wherein R is hydrogen or alkyl of 2 to 6 carbon atoms.

The preferred compounds of formula I wherein R is alkyl of 2 to 6 carbon atoms, are those wherein R contains 2 to 4, especially 2 or 3 carbon atoms, or wherein R is branched, especially in an α position to the nitrogen atom to which R is bound.

R especially signifies isopropyl.

Further, in accordance with the invention a compound of formula I may be obtained by a process comprising condensing a reactive functional derivative of an acid of formula II,

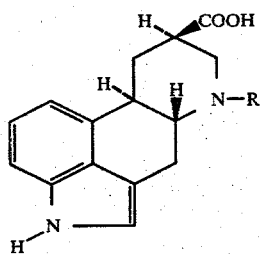

wherein R is as defined above, with the compound of formula III

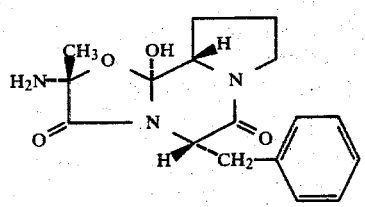

in the form of a salt.

The compounds of formula I are peptide ergot alkaloids. The reaction of the invention is a condensation reaction for amides. The process of the invention may be effected in a manner analogous to known methods for the production of structurally similar peptide alkaloids.

The reaction is effected in an inert organic solvent or solvent mixture and in the presence of an acid-binding agent. The condensation is conveniently effected at a temperature between −30° and +20° C.

1.2 to 2.4 mols of a reactive derivative of an acid of formula II are conveniently used for every mol of the compound of formula III in salt form.

An example of a suitable reactive derivative of an acid of formula II is the addition product resulting from the reaction of an acid of formula II with a chlorinating agent and an N-di(lower)alkyl-substituted acid amide of an aliphatic carboxylic acid of 1 to 3 carbon atoms, such as dimethyl formamide or dimethyl acetamide.

Thionyl chloride, phosgene or oxalyl chloride may, for example, be used as chlorinating agent.

Examples of suitable inert solvents for the reaction are: chlorinated aliphatic hydrocarbons, such as chloroform or methylene chloride, N-di(lower)alkyl-substituted acid amides of aliphatic carboxylic acids, such as dimethyl formamide, or other organic solvents, e.g. acetonitrile.

Tertiary organic bases, e.g. triethylamine, preferably pyridine, are conveniently used as condensation agents.

In place of the above mentioned addition product it is also possible to use other reactive derivatives of an acid of formula II for the reaction, e.g. the acid chloride hydrochloride, the acid azide, or mixed anhydrides of an acid of formula II with sulphuric or trifluoroacetic acid. However, 6-nor-9,10-dihydrolysergic acid is preferably activated with dimethyl formamide/oxalyl chloride.

The production of these reactive derivatives of an acid of formula II may be effected in a manner analogous to known methods, using the corresponding acid.

The working up and isolation are effected in accordance with known methods.

Acid addition salt forms may be produced from the free base forms in known manner and vice versa. Suitable acids for salt formation include methane sulphonic acid and malic acid.

Of the compounds of formula II 6-nor-9,10-dihydrolysergic acid and 6-nor-6-ethyl-9,10-dihydrolysergic acid are known [Helv.chim.Acta 53, 2197 f (1970)].

The new compounds of formula IIa,

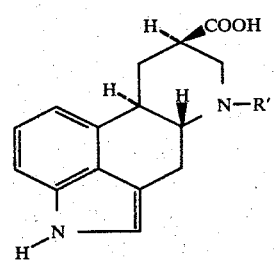

wherein R' is alkyl of 3 to 6 carbon atoms, are obtained by hydrolyzing a compound of formula IV,

[Formula IV structure]

wherein
  R' is as defined above, and
  R₁ is a radical capable of being split off hydrolytically.

R₁ may, for example, signify lower alkyl, e.g. methyl or ethyl.

The compounds of formula IIa are valuable intermediates for the production of pharmacodynamically active 6-nor-6-R'-ergolines wherein R' is as defined above, for example of 6-nor-6-R'-9,10-dihydro-2'β-methyl-5'α-benzyl-ergopeptine compounds wherein R' is as defined above.

The hydrolysis of compounds of formula IV may be effected in a manner analogous to known methods for the hydrolysis of lysergic acid esters.

The hydrolysis is conveniently effected under alkaline conditions, for example by treating a solution of a compound of formula IV in a water-miscible organic solvent or solvent mixture with an alkali metal hydroxide, e.g. caustic soda solution.

A suitable solvent is, for example, an ether such as dioxane or tetrahydrofuran, or an alkanol such as methanol, and a suitable solvent mixture is, for example, methanol/methylene chloride.

The reaction is effected under mild conditions. When the reaction is effected at room temperature, it has a duration of approximately 24 hours.

The compounds of formula IV are obtained by alkylation of a compound of formula V,

[Formula V structure]

wherein R₁ is as defined above.

The alkylation may be effected in a manner analogous to known methods, e.g. as described in Helv. chim. Acta 53, 2197 f (1970). This literature also indicates or describes suitable demethylation methods for the production of 6-nor-lysergic acid esters. The compounds of formula V are obtained in analogous manner by demethylation of a compound of formula VI,

[Formula VI structure]

wherein R₁ is as defined above.

Insofar as the production of the starting materials is not described, these are known or may be produced in accordance with known processes or in a manner analogous to known processes.

6-Nor-9,10-dihydro-2'β-methyl-5'α-benzyl-ergopeptine is a valuable starting material for the production of 9,10-dihydro-2'β-methyl-5'α-benzyl-ergopeptine derivatives, e.g. of 6-nor-6-alkyl-9,10-dihydro-2'β-methyl-5'α-benzyl-ergopeptine compounds such as dihydroergotamine. The latter compounds are obtained by alkylation of the corresponding 6-nor compounds, e.g. as described for the alkylation of compounds of formula V.

The name of the compounds of formula I is derived from the basic structure of formula VII,

[Formula VII structure]

which is named ergopeptine for purposes of simplification.

In the following non-limitative Examples all temperatures are indicated in degrees centigrade.

EXAMPLE 1

6-nor-6-isopropyl-9,10-dihydro-2'β-methyl-5'α-benzyl-ergopeptine (compound of formula I)

8.6 cc (100 millimols) of oxalyl chloride dissolved in 20 cc of acetonitrile are added dropwise at −10° to −15° within 10 minutes to a solution of 300 cc of dimethyl formamide and 150 cc of acetonitrile, and stirring is effected for a further 10 minutes. 30 g (100 millimols) of anhydrous 6-nor-6-isopropyl-9,10-dihydrolysergic acid are subsequently sprinkled in at −20°, and stirring is effected at −10° for 30 minutes. After cooling to −20°, 200 cc of pyridine and 29.4 g (80 millimols) of (2R,5S,10aS,10bS)-2-amino-2-methyl-5-benzyl-3,6-dioxo-10b-hydroxy-octahydro-8H-oxazolo[3,2-a]pyrrolo[2,1-c]pyrazine hydrochloride are added, and stirring is effected at 0° for 2 hours. Working up is effected by adding 100 cc of a buffer solution pH=4 and dividing the reaction mixture between methylene chloride and a 2 N caustic soda solution. The organic phases are washed twice with water, dried over sodium sulphate and evaporated to dryness on a rotary evaporator. After drying in a high vacuum the resulting crude base is dissolved in approximately 150 cc of ethanol and the solution is seeded. The pure crystalline title compound has an M.P. of 225° (decomp.), $[\alpha]_D^{20} = -40.5°$ (c=0.930 in methylene chloride).

Production of the methane sulphonate 17 g of pure 6-nor-6-isopropyl-9,10-dihydro-2'β-methyl-5'α-benzyl-ergopeptine are dissolved in 1 liter of acetone, and 2.67 g of methanesulphonic acid are added. Concentration to approximately ¼ of the original volume leads to crystallization.

Filtration and washing with acetone yield a pure methane sulphonate having an M.P. of 206°-208° (decomp.), $[\alpha]_D^{20} = -23.5°$ (c=0.5 in methanol).

In analogous manner the hydrogen malate salt form is obtained, M.P. 202° (dec. H.v.) $[\alpha]_D^{20} = -24°$ (c=0.5 in CH₃OH).

The following compounds of formula I are obtained in a manner analogous to that described in Example 1 by using the corresponding starting materials of formula II and of formula III in salt form:

| | Compound of formula I | | | From the compound of formula II having an |
|---|---|---|---|---|
| Example | R | M.P. | $[\alpha]_D^{20}$ | M.P. |
| 2 | isobutyl | 175°-176° (decomp.) | -44.9° (c = 0.862 in methyl.) | 234°-235° (dec., Hv) $[\alpha]_D^{20} = -100°$ (C = 0.989, pyridine) |
| 3 | ethyl | 208° (decomp.) | -29.9° c = 0.473 in dimethyl sulphoxide | 305° (dec., Hv) $[\alpha]_D^{20} = -78°$ (c = 0.5 in dimethyl sulphoxide) |
| 4 | n-propyl | 194° (decomp.) | -23.3° (c = 0.476 in dimethyl sulphoxide | 213°-214° (dec., Hv) $[\alpha]_D^{20} = -61°$ (c = 0.5 in dimethyl sulphoxide) |
| 5 | H | 184° | -12.3° (c = 0.881 in methanol) | 341°-345° (dec., Hv) $[\alpha]_D^{20} = -40°$ (c = 1 in 0.1 N NaOH) |

EXAMPLE 6

6-nor-6-isopropyl-9,10-dihydrolysergic acid (compound of formula IIa)

34.6 g (0.111 mols) of 6-nor-6-isopropyl-9,10-dihydrolysergic acid methyl ester are dissolved in 600 cc of methanol and 100 cc of methylene chloride, and 100 cc of a 2 N caustic soda solution are added. After stirring over night at room temperature the organic solvents are removed on a rotary evaporator, and the residue is diluted with 1 liter of water. The pH of the solution is adjusted to 5 with glacial acetic acid, whereby the acid is obtained as jelly-like lump. Heating to 80° gives a clear solution, from which the acid crystallizes upon cooling. Drying in a high vacuum at 130° leads to the anhydrous title compound having an M.P. of 290° (decomp.), $[\alpha]_D^{20} = -101°$ (c=0.6 in methanol).

The compounds of formula II characterized in the above Table are obtained in a manner analogous to Example 6 by hydrolysis of the corresponding ester.

EXAMPLE 7

6-nor-6-isopropyl-9,10-dihydrolysergic acid methyl ester (compound of formula IV)

40 g (0.148 mols) of 6-nor-9,10-dihydrolysergic acid methyl ester are dissolved in 400 cc of dimethyl formamide, 61 g of anhydrous potassium carbonate and 139 cc (1.48 mols) of isopropyl bromide are added, and heating is effected to 80° with stirring for 48 hours. After working up and purification the title compound crystallizes from ethanol in the form of colourless crystals having an M.P. of 194°, $[\alpha]_D^{20} = -80.2°$ (c=0.582 in methanol).

The compounds of formula I are useful as venoconstrictors and venotonic agents, e.g. for the treatment of orthostatic disorders, e.g. peripheral vascular disorders, as indicated by a pressor effect of long duration in the spinalized cat accompanied by a rise in blood pressure on i.v. administration of from about 0.02 mg to about 0.05 mg/kg animal body weight of the compounds.

For this use the dosage will, of course, vary depending on the compound employed, mode of administration and treatment desired. However, in general, satisfactory results are obtained when administered at a daily dosage of from about 0.02 mg to about 0.2 mg per kg animal body weight, conveniently given in divided doses 2 to 4 times a day or in sustained release form. For the larger mammals, the total daily dosage is in the range from about 1.5 to about 15 mg, and dosage forms suitable for oral administration comprise from about 0.4 mg to about 7.5 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

In one group of compounds R is hydrogen. In another group of compounds R is alkyl.

6-Nor-6-isopropyl-9,10-dihydro-2'β-methyl-5'α-benzyl-ergopeptine has been found to be especially interesting as well as the corresponding 6-nor-6-ethyl and 6-nor-6-propyl compound.

What we claim is:

1. A compound of the formula I,

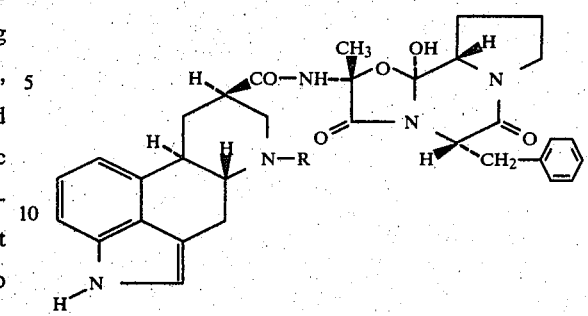

wherein R is a branched chain alkyl of 3 to 6 carbon atoms, or a pharmaceutically acceptable acid addition salt thereof.

2. The compound of claim 1 which is 6-nor-6-isopropyl-9,10-dihydro-2'β-methyl-5'α-benzyl-ergopeptine.

3. The compound of claim 1 wherein R is iso-butyl.

4. A pharmaceutical composition useful in treating vascular disorders comprising a therapeutically effective amount of a compound of claim 1 in association with a pharmaceutical carrier or diluent.

5. A method of treating peripheral vascular disorders in animals, which comprises administering to an animal in need of such treatment a therapeutically effective amount of a compound of claim 1.

6. A compound according to claim 1 wherein R is alkyl of 3 or 4 carbon atoms.

7. The compound of claim 1 wherein R is branched at the α-position to the nitrogen atom to which R is attached.

* * * * *